United States Patent [19]
Smith

[11] Patent Number: 6,145,503
[45] Date of Patent: Nov. 14, 2000

[54] OLFACTORY ACTIVATOR

[76] Inventor: Ronnie Smith, Rte.-1 Box 67, Alum Creek, W. Va. 25003-9503

[21] Appl. No.: 09/114,094

[22] Filed: Jul. 13, 1998

[51] Int. Cl.⁷ .................................................. A61M 15/00
[52] U.S. Cl. ................................ 128/202.16; 128/200.24
[58] Field of Search ........................ 128/202.16, 200.24, 128/200.27, 205.19, 202.21, 203.18; 73/23.34; 482/13; 261/DIG. 65

[56] References Cited

U.S. PATENT DOCUMENTS

| | | | |
|---|---|---|---|
| 4,832,042 | 5/1989 | Poppendiek et al. ............... | 128/205.19 |
| 4,971,053 | 11/1990 | Tarrats ................................ | 128/205.19 |
| 5,211,171 | 5/1993 | Choromokos ...................... | 128/205.19 |
| 5,313,821 | 5/1994 | Bett et al. . | |
| 5,522,253 | 6/1996 | Knight .................................. | 73/23.34 |
| 5,647,345 | 7/1997 | Saul .................................... | 128/201.23 |
| 5,649,533 | 7/1997 | Oren . | |
| 5,904,140 | 5/1999 | McGoogan .......................... | 128/200.24 |

*Primary Examiner*—Aaron J. Lewis
*Assistant Examiner*—Teena Mitchell
*Attorney, Agent, or Firm*—Robert N. Blackmon

[57] ABSTRACT

A method and device for activating olfactory senses by drawing air and air-born aroma across the olfactory nerves. Creating airflow to activate olfactory sensation by pulling air and aromas over the olfactory nerves is accomplished by drawing air out throw a patient's mouth. Since the oral cavity and the nasal cavity are connected, this effectively draws air through the a person's nose in a manner simulative of natural breathing. A device has a mouthpiece with an air conduit therethrough, and a mechanism for drawing air through the mouthpiece. The mechanism may be an impeller driven by a motor, which may be locally powered by batteries. A filter may be provided in the mouthpiece or interposed between the mouthpiece and the air drawing mechanism to catch saliva drawn through the mouthpiece. The method and device allows patients with insufficient airflow, such as due to a tracheotomy, to experience olfactory sensations. These sensations, namely smell and taste, improve appetite and overall quality of life.

15 Claims, 2 Drawing Sheets

OLFACTORY ACTIVATOR

BACKGROUND OF THE INVENTION

1. Field of the Invention

The present invention relates to sensory activation and enhancement. More specifically, the invention provides methods and devices that activate and enhance olfactory function.

2. Description of the Prior Art

A tracheotomy is a surgical procedure where an incision is made in the front of the neck and a breathing tube is placed into the windpipe. Tracheotomies are performed when there is an upper airway obstruction from swelling, blood, or foreign matter. Many times this is an emergency operation to restore oxygen flow to the lungs when more benign methods, such as the insertion of an endotracheal tube without incision, are unsuccessful. Various conditions, including laryngeal or maxillofacial trauma, laryngotracheal separation, hematoma, edema, tumor, abscess, pneumonia, bronchoiectasis, severe sleep apnea, or advanced emphysema may indicate tracheotomies.

Though effective in preventing suffocation from lack of oxygen, tracheotomies have the unfortunate side-effect of cutting off inward airflow through a patient's nose, normally created by a negative pressure gradient between a patient's lungs and ambient air. Since olfactory nerve receptors in the nose are only activated when air-born particles are brought into contact with the olfactory epithelium by such airflow, the senses of smell and to a significant degree taste are compromised. Concomitant loss of appetite may occur with the loss of smell and taste.

One prior art solution to this problem is described by U.S. Pat. No. 5,522,253, issued Jun. 4, 1996 to Roy F. Knight. In this patent, a variety of devices are provided in which air is forced into the nasal cavity by a bulbous pump or a system of tubes connected to an automatic pump. These devices are highly directional, where a portion of the device is placed in close proximity to a source of an aroma. Further, another portion of the device is inserted into the nose, which may be objectionable to the user.

U.S. Pat. No. 5,313,821, issued May 24, 1994 to Karen L. Bett et al. describes an apparatus for evaluating aromas that includes a filter which substantially blocks air-born particles. Again, this apparatus is adapted to force air into the nose. U.S. Pat. No. 5,649,533, issued Jul. 22, 1997 to Nathan Oren describes a therapeutic respiration device that includes a pair of diaphragm-type one way valves for regulating breathing. This device, in addition to being placed over the nose like the other prior art described, does not provide, but merely regulates airflow.

None of the above inventions and patents, taken either singly or in combination, is seen to describe the instant invention as claimed.

SUMMARY OF THE INVENTION

The present invention provides a method of creating airflow to activate olfactory sensation by pulling air and aromas over the olfactory nerves. This is accomplished by drawing air out through a patient's mouth. Since the oral cavity and the nasal cavity are connected, this effectively draws air through the patient's nose in a manner more simulative of airflow drawn from natural breathing.

A device according to the present invention includes a mouthpiece having an air conduit therethrough, and a mechanism for drawing air through the mouthpiece. An impeller driven by a motor, which may be locally powered, is preferably employed as an air drawing mechanism. The air drawing mechanism may alternatively be an air pump, such as those including piston, diaphragm or bellows to pump air. A filter may be provided in the mouthpiece or interposed between the mouthpiece and the air drawing mechanism to catch saliva drawn through the mouthpiece.

Accordingly, it is one object of the invention to provide a method and device for activating olfactory senses by drawing air and air-born aroma across the olfactory nerves.

It is another object of the invention to provide a method and device which draws air through the mouth, such that airflow may be created between the mouth, oral cavity, nasal cavity, and nose of an user in a natural manner simulative of breathing.

It is a further object of the invention to provide a device including a mouthpiece and a mechanism for drawing air through the mouthpiece.

Still another object of the invention is to provide such a device which includes an impeller, a motor driving the impeller, and a power source powering the motor together in a compact assembly which may be hand-held.

These and other objects of the present invention will become readily apparent upon further review of the following specification and drawings.

BRIEF DESCRIPTION OF THE DRAWINGS

Other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
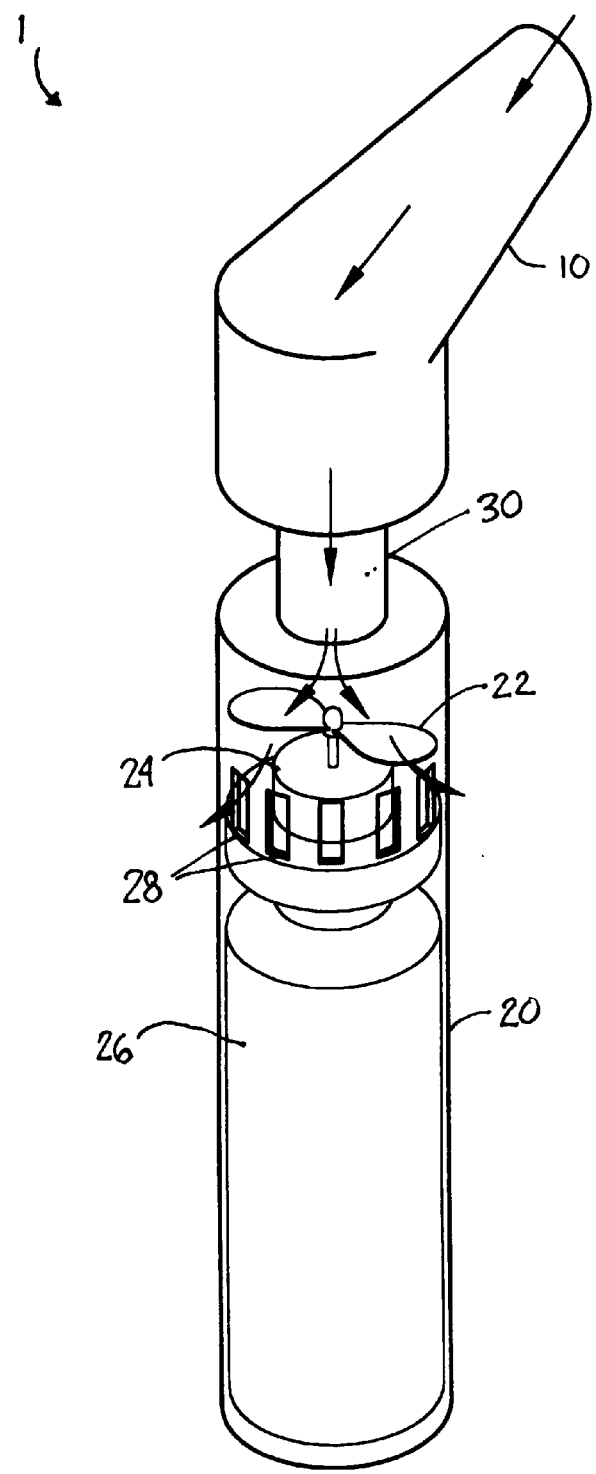
FIG. 1 is a perspective view showing an embodiment of a device according to the invention.

Turning now to FIG. 1 of the drawings, a preferred olfactory activating device 1 for practicing the present method is provided. This device includes a mouthpiece 10 and an air drawing mechanism. The air drawing mechanism preferably includes an impeller 22 rotatably mounted in an assembly casing 20. The assembly casing further contains a drive motor 24 for driving the impeller, and a power source 26 for powering drive motor 24. Air vents 28 are provided to allow air to exit the casing. A filter element 30 is preferably provided to catch saliva, and may be disposed in the mouthpiece, or in the casing upflow of the impeller as shown.

Mouthpiece 10 has an air conduit defined therethrough, such that air may be drawn in the direction of arrows depicted. Preferably, the mouthpiece includes an angled section as shown. The mouthpiece may be made unitarily with the casing. However, it is preferable that the mouthpiece be detachably secured to the casing to provide access to the filter element 30. A detachable mouthpiece may also be easily replaced should it become fouled or for other sanitary considerations such as to allow use by others.

The filter element 30, when present, may be of any type which substantially traps saliva, but allows air to pass therethrough. Fine pore filter elements can be used, such as those with pores in the micron to submicron range. In this manner saliva will be held in its fluid state on one side of the filter element. Alternatively, the filter element may be of the absorbent type in which saliva is trapped within the filter element. Filter elements which may be cleaned and reused are preferred, though disposable elements are also contemplated.

Breathing normally can draw between about a 0.5 liter to several liters of air into the lungs per breath, depending on the individual and the depth of breath taken. Accordingly, the present invention may be adapted to draw through the mouth a similar volume per unit time by selecting an appropriate air drawing mechanism, thereby simulating the quantity of aromas which would be perceived by natural breathing. For example, impeller shape and/or size, as well as the rotational rate at which the impeller is driven, may be selected to provide up to about 1.5 liters of air per second. Most preferably, the rate is at least 0.1 liter per second. The device of the invention may be provided with adjustable controls (not shown) for rotational rates to best suit each individual. An activating button or the like (not shown) may be used either for switching the motor between on and off positions, and/or between various motor speeds. An activating button in which finger actuated pressure is required for operation of the device is another preferred arrangement.

Figure 2:
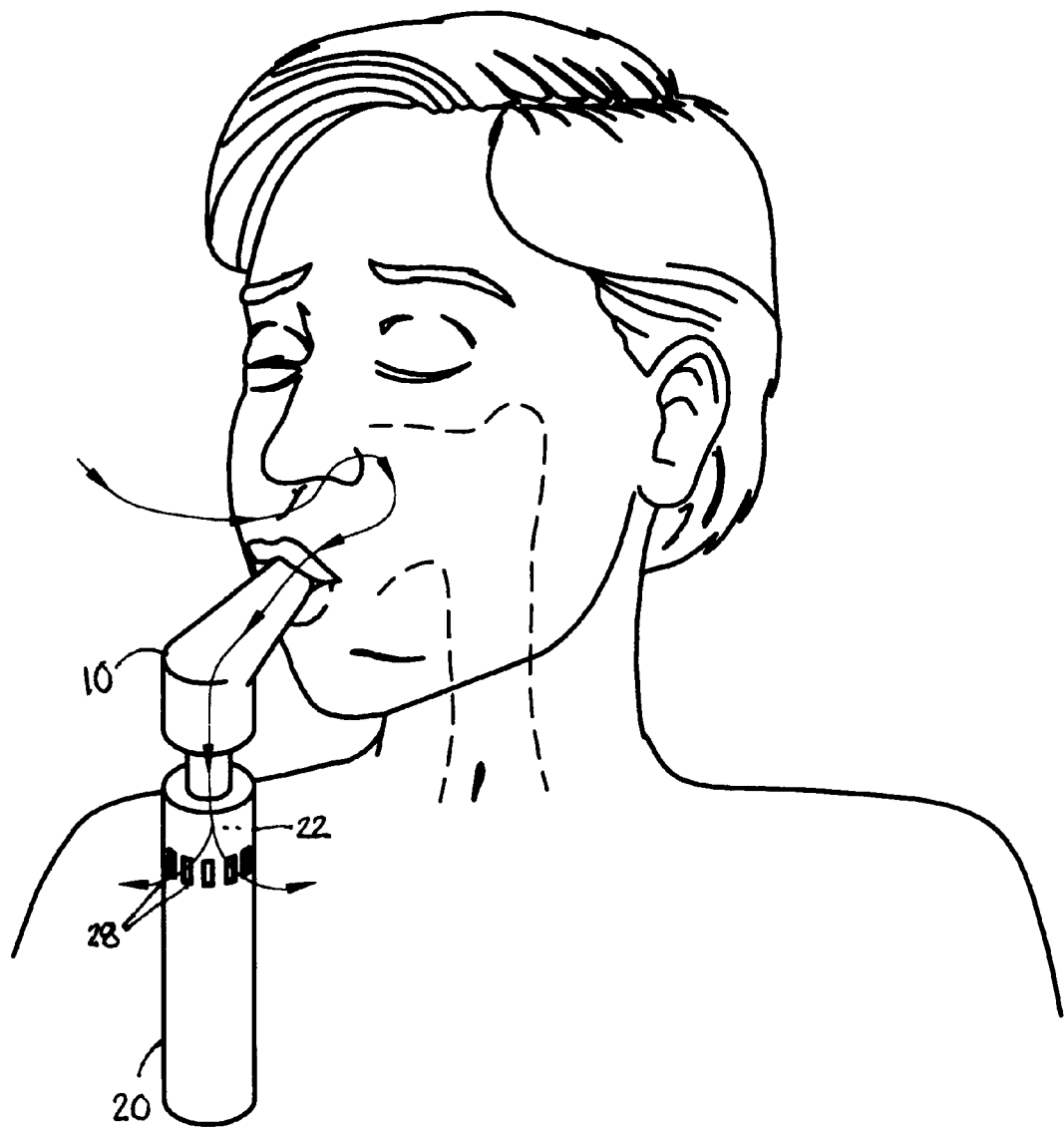
FIG. 2 is an environmental view showing the device of FIG. 1 employed in a method according to the present invention.

Turning to FIG. 2, the method of the present invention is shown. The device of FIG. 1 is held such that the mouthpiece is proximate the mouth of a person. The device is activated and air is drawn through the oral cavity and the mouthpiece 10 of the device by the action of impeller 22, finally exiting through vents 28 in the device's assembly casing. This in turn draws air through the person's nose, into the person's nasal cavity, where any air-born aromas are brought into contact with olfactory nerves therein. Filter element 30 traps saliva so that the air drawing mechanism is not adversely effected.

It is to be understood that the present invention is not limited to the embodiments described above, but encompasses any and all embodiments within the scope of the following claims.

I claim:

1. A method to stimulate appetite, for activating olfactory sensation in a person having insufficient airflow over olfactory nerves in a person's nasal cavity to produce such sensation, said method comprising the steps of:
   a) inserting a mouthpiece of a suction device into a mouth of a person,
   b) activating said suction device to draw air inwardly through a nose of a person and outwardly through a person's mouth through said mouthpiece,
   thereby accordingly drawing air and air born aromas over a person's olfactory nerves in a person's nasal cavity to stimulate olfactory sensation.

2. The method according to claim 1 wherein said insufficient air flow is an effect of a tracheotomy, and said suction mechanism is used to stimulate the olfactory sensation in a tracheotomy patient.

3. The method according to claim 1 wherein the step of drawing air through a person's mouth is performed at a rate of normal breathing.

4. The method according to claim 3 wherein said rate is between about 0.1 and 1.5 liters per second.

5. The method according to claim 1 wherein said device selected includes said mouthpiece mounted to one end of an assembly casing, said casing further containing an impeller rotatably mounted to draw air from said mouthpiece, a motor driving said impeller, and a power source powering said motor.

6. A device for stimulating appetite by activating olfactory sensation in a person having insufficient airflow over olfactory nerves in a person's nasal cavity to produce such sensation, said device comprising a mouthpiece having a conduit therethrough and suction means in communication with said conduit for drawing air in through a nose of a person and outwardly through a person's mouth through said mouthpiece and accordingly drawing air and air born aromas over a person's olfactory nerves in a nasal cavity.

7. The device according to claim 6 wherein said insufficient air flow is an effect of a tracheotomy.

8. The device according to claim 6 further comprising a filter for filtering saliva, said filter disposed upflow from said mechanism for drawing air.

9. The device according to claim 6 wherein said device further includes an assembly casing, said mouthpiece mounted to one end of said assembly casing, said assembly casing containing an impeller rotatably mounted to draw air from said mouthpiece, a motor for driving said impeller, and a power source powering said motor.

10. The device according to claim 9 further comprising a saliva filter mounted in said casing upflow said impeller.

11. The device according to claim 9 further comprising a saliva filter mounted in said conduit of said mouthpiece.

12. The device according to claim 9 further comprising an adjustable control for varying the power from said power source to said motor.

13. The device according to claim 9 wherein said power source comprises at least one D.C. battery.

14. The device according to claim 9 wherein the impeller is driven to draw air through a person's mouth at a rate of normal breathing.

15. The method according to claim 9 wherein said rate is between about 0.1 and 1.5 liters per second.

\* \* \* \* \*